United States Patent [19]

Miyoshi et al.

[11] Patent Number: 4,800,268

[45] Date of Patent: Jan. 24, 1989

[54] METHOD AND APPARATUS FOR SCANNING A LASER BEAM TO EXAMINE THE SURFACE OF SEMICONDUCTOR WAFER

[75] Inventors: Motosuke Miyoshi, Tokyo; Katsuya Okumura; Shigeru Ogawa, both of Yokohama, all of Japan

[73] Assignee: Kabushiki Kaisha Toshiba, Kawasaki, Japan

[21] Appl. No.: 91,867

[22] Filed: Sep. 1, 1987

[30] Foreign Application Priority Data

Sep. 17, 1986 [JP] Japan ................... 61-218434

[51] Int. Cl.$^4$ ................................. H01J 3/14
[52] U.S. Cl. ..................... 250/234; 350/6.7
[58] Field of Search ............... 250/548, 557, 234, 235, 250/236, 571, 572; 356/400, 401; 350/6.7, 6.8

[56] References Cited

U.S. PATENT DOCUMENTS

| | | | |
|---|---|---|---|
| 4,367,952 | 1/1983 | Ahrens et al. | 356/400 |
| 4,539,481 | 9/1985 | Troukens et al. | 250/557 |
| 4,677,301 | 6/1987 | Tanimoto et al. | 250/548 |
| 4,682,037 | 7/1987 | Kosugi | 250/548 |
| 4,710,029 | 12/1987 | Katoh | 356/401 |

Primary Examiner—David C. Nelms
Assistant Examiner—William Oen
Attorney, Agent, or Firm—Finnegan, Henderson, Farabow, Garrett, & Dunner

[57] ABSTRACT

An apparatus for scanning a laser beam to examine the surface of a semiconductor wafer comprises a stage onto which a semiconductor wafer is mounted and a laser beam scanning unit for repeatedly rectilinearly scanning a laser beam in a predetermined direction on the semiconductor wafer. This scanning apparatus further has a drive unit for rotating the semiconductor wafer and for moving the semiconductor wafer by only a predetermined distance in the predetermined direction every rotation of the wafer. The laser beam scanning unit rectilinearly scans the laser beam at a swing width of a predetermined amount.

5 Claims, 3 Drawing Sheets

METHOD AND APPARATUS FOR SCANNING A LASER BEAM TO EXAMINE THE SURFACE OF SEMICONDUCTOR WAFER

BACKGROUND OF THE INVENTION

The present invention relates to a method and apparatus for scanning a laser beam onto a semiconductor wafer to examine the surface of the semiconductor wafer prior to manufacturing a semiconductor device.

To detect microparticles (dust and the like) attached to the surface of the semiconductor wafer and any defects formed on the surface, the wafer surface is scanned by a focused laser beam having a small diameter, thereby detecting the light which is scattered by the micorparticles and defective portions. In this case, hitherto, a method of scanning the laser beam has been mainly classified into the following two kinds of methods. (1) In the first method, the optical system to irradiate a laser beam is fixed and, as shown in FIG. 1, a stage on which wafer 11 is mounted is gradually rectilinearly moved in constant direction X while rotating in rotational direction $\theta$, so that a laser beam is scanned on wafer 11 so as to draw spiral locus A. (2) In the second method, as shown in FIG. 2, the stage on which wafer 11 is mounted is fixed and a laser beam is raster scanned on wafer 11 in the X and Y directions. Or, the laser beam is scanned on wafer 11 in the X direction perpendicular to the Y direction while moving the stage in constant direction Y so as to eventually draw such a locus as shown by B in the diagram. The laser beam scanning can be realized by irradiating laser beam 1 on polygon mirror 2 and by using the reflection of the laser beam by this mirror.

In the conventional wafer surface examining technique, a spot diameter of the laser beam on the irradiating surface is set to about 100 $\mu$m and the maximum detecting sensitivity is set to a value from 0.3 to 0.5 $\mu$m$\phi$ ($\phi$ denotes a diameter of the detected particle). In the case of scanning the whole surface of the wafer by use of the laser beam having such a spot diameter, the problems of the measuring time (time required for scanning) and the design technique of the optical system can be relatively easily solved. On the other hand, the sizes of the dust particles and the defects to be detected have steadily decreased in association with the advance of the technique of finding a wafer pattern, and therefore, an increased detecting sensitivity is required. As the most effective method of satisfying such a requirement, there is a method whereby a diameter of a laser beam is converged into a small diameter to thereby increase the irradiation light intensity per unit area. For example, to obtain the detecting sensitivity of 0.1 $\mu$m$\phi$, it is necessary to reduce the beam spot diameter to 10 $\mu$m. However, in the foregoing conventional laser beam scanning methods, in the case of reducing the beam spot diameter, the following problems are caused. (1) In the method of spirally scanning the laser beam, the scan distance inevitably becomes long due to the reduction in the beam spot diameter and the measuring time, i.e., the scanning time becomes long, resulting in a loss of practical use efficiency. (2) In the case of scanning the beam on the whole surface of the wafer in the X and Y directions, the scanning distance, i.e., the swing width is increased. As a diameter of a wafer increases in the future, the swing width increases more and more. To reduce the beam spot diameter to 10 $\mu$m, a demagnification optical system is needed. However, when the swing width is increased, the aberration also increases, so that it is difficult to reduce the beam spot diameter. On the other hand, the illuminance in the spot varies, depending on the irradiating position of the spot, resulting in a deterioration in the detecting accuracy. In addition, when the swing width is large, even if the beam spot is a true circle at the center of the wafer, the cross section of the beam becomes an ellipse at the edge portion of the wafer. This means that the detecting sensitivity differs depending on the measuring position on the wafer.

SUMMARY OF THE INVENTION

It is an object of the present invention to provide a method and apparatus for scanning a laser beam to examine the surface of a semiconductor wafer in which the whole surface of the wafer can be scanned for a short time at a high detecting sensitivity.

This object is accomplished by an apparatus for scanning a laser beam to examine the surface of a semiconductor wafer comprising a stage onto which a semiconductor wafer is mounted, a driving unit for rotating the semiconductor wafer and for moving the semiconductor wafer by a predetermined distance in a predetermined direction for each rotation of the wafer, and a laser beam scanning unit for repeatedly rectilinearly scanning the laser beam at a swing width of a predetermined amount in the predetermined direction on the semiconductor wafer.

According to the scanning apparatus of the present invention, the stage is rotated and is simultaneously rectilinearly moved by a constant amount in a constant direction for each rotation. The polygon mirror repeatedly rectilinearly scans the laser beam at a swing width of a constant amount. Complicated mechanisms of the mechanical and optical systems are not needed to realize the synchronized operations of the stage and laser beam, so that this scanning apparatus can be technically easily accomplished.

Further, the above object is accomplished by a method of scanning a laser beam to examine the surface of a semiconductor wafer comprising the steps of rotating a semiconductor wafer; repeatedly rectilnearly scanning a laser beam on the surface of the semiconductor wafer at a constant swing width in the direction perpendicular to the rotational direction of the semiconductor wafer; and moving the semiconductor wafer by a predetermined distance in the same or opposite direction as the scanning direction each time the semiconductor wafer rotates once, thereby substantially spirally scanning the laser beam on the surface of the semiconductor wafer.

According to the scanning method of the present invention, since the laser beam spot is repeatedly rectilinearly scanned on the wafer at a swing width of a constant amount and at the same time, it is eventually scanned at a predetermined width in the rotational direction of the wafer in association with the rotation of the wafer. Therefore, even when the beam spot diameter is reduced, the whole surface of the wafer can be substantially spirally scanned in a short time. In this case, it is sufficient to set a swing width of the beam to be shorter than the diameter of a wafer. A problem rarely occurs due to a change in beam shape or beam spot diameter depending on the beam scanning position. The detecting sensitivity of the wafer surface does not vary with the beam scanning position but becomes uniform.

DETAILED DESCRIPTION OF THE PREFERRED EMBODIMENT

Figure 1:
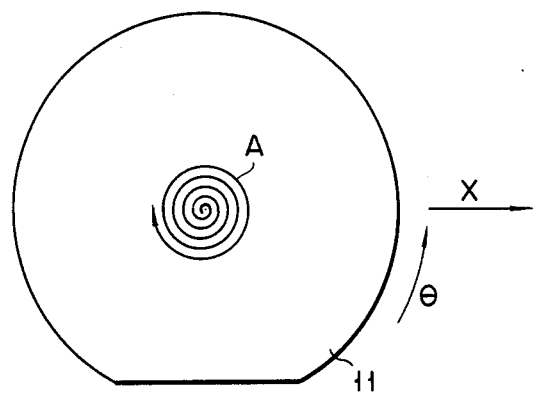
FIG. 1 shows a scanning pattern which is obtained by a conventional laser beam scanning method of spirally scanning a laser beam on a wafer.
Figure 2:
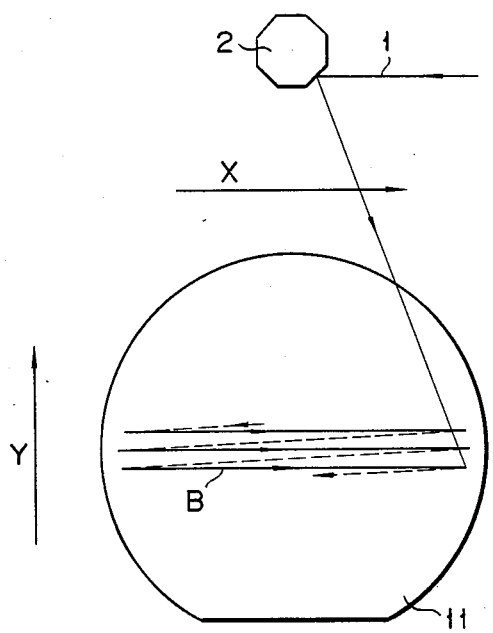
FIG. 2 shows a scanning pattern which is obtained by a conventional laser beam scanning method of scanning a laser beam on a wafer in the direction of an axis of ordinate.
Figure 3:
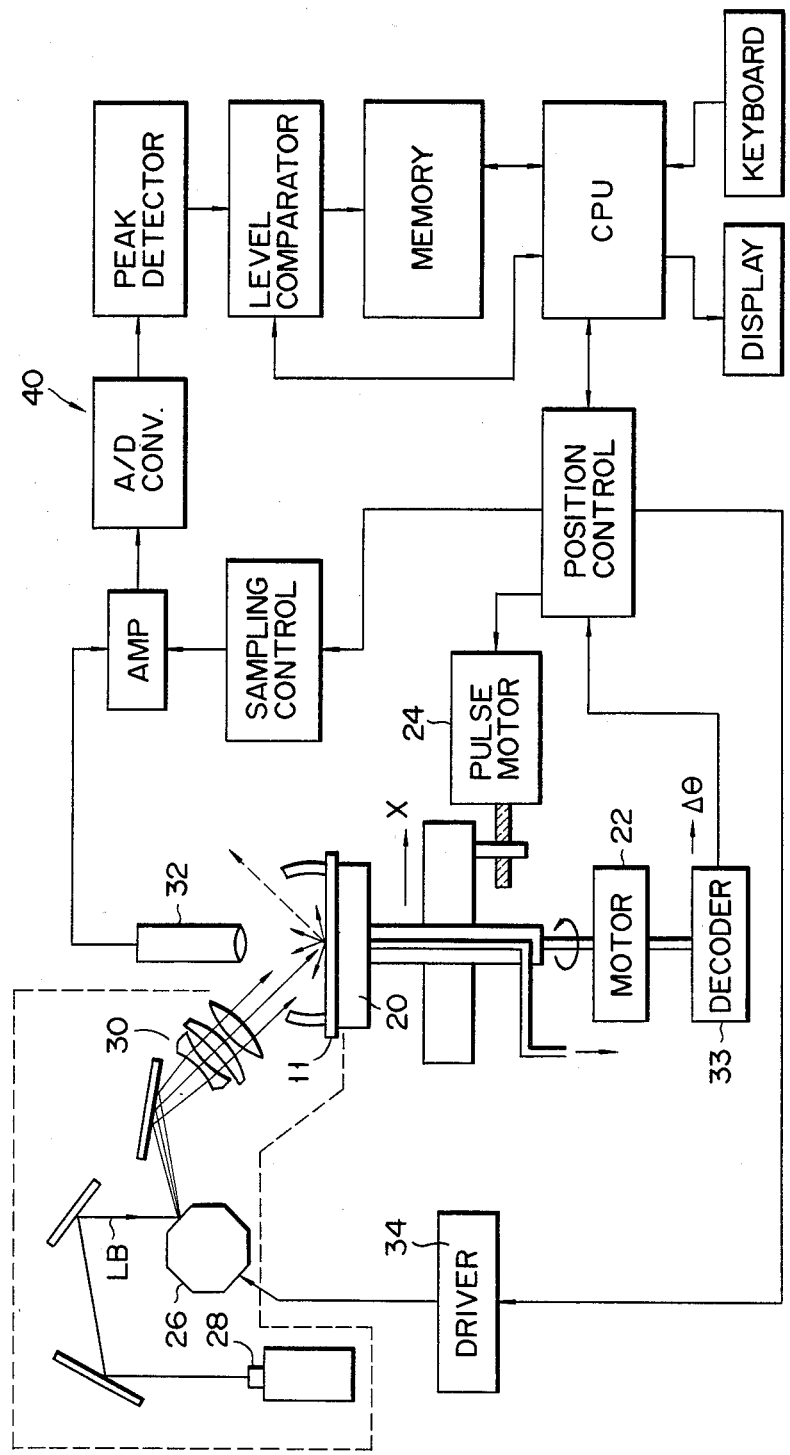
FIGS. 3 and 4 are diagrams schematically showing a constitution of a laser beam scanning apparatus according to an embodiment of the present invention.
Figure 4:
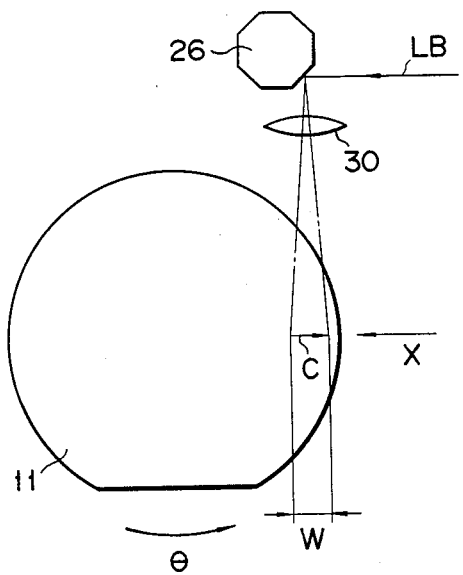

FIGS. 3 and 4 schematically show an apparatus for scanning a laser beam to examine the surface of a semiconductor wafer according to an embodiment of the present invention. This scanning apparatus includes: stage 20 on which semiconductor wafer 11 to be examined is mounted; drive motor 22 to rotate stage 20; and pulse motor 24 for rectilinearly moving stage 20 by a predetermined distance for each rotation in predetermined direction X along the semiconductor wafer surface.

Laser beam LB is generated from Ar ion laser generator 28 and reflected by a reflecting mirror. After laser beam LB is reflected by the reflecting surface of polygon mirror 26, it is irradiated onto the surface of semiconductor wafer 11 through focusing lens system 30. A part of the laser beam reflected by the semiconductor wafer surface is detected by optical multiplier or beam detector 32. An output signal of detector 32 is processed by control system 40 including a CPU, a position detector, and the like. Polygon mirror 26 is rotated at a predetermined speed by driver 34 and is arranged so as to scan the laser beam onto line segments having predetermined length W in a predetermined direction on wafer 11, preferably, in a predetermined direction passing through the rotational center of wafer 11. For example, when polygon mirror 26 has eight reflecting surfaces, each time mirror 26 rotates once, the line scan of predetermined length W is executed eight times. Focusing lens system 30 includes, e.g., an fθ lens and focuses the laser beam reflected by polygon mirror 26 onto the surface of wafer 11. Thus, even when the laser beam in scanned onto the surface of wafer 11 by the rotation of polygon mirror 26, the shape and diameter of the spot of the laser beam irradiated onto the semiconductor wafer surface do not vary. Each time a single rotation of stage 20 is detected on the basis of rotational angle information from encoder 33, a drive signal is supplied to pulse motor 24 for position control by control system 40, thereby moving stage 20 by predetermined distance W in predetermined direction X. Further, whenever the rotation of stage 20 corresponding to the angle of $\Delta\theta$ is detected on the basis of the angle information from encoder 33, the position control rotates polygon mirror 26 by a predetermined angle so that the laser beam is scanned once.

A laser beam scanning method and a semiconductor wafer surface examining method using the laser beam scanning apparatus shown in FIGS. 3 and 4 will now be described hereinbelow.

Figure 5:
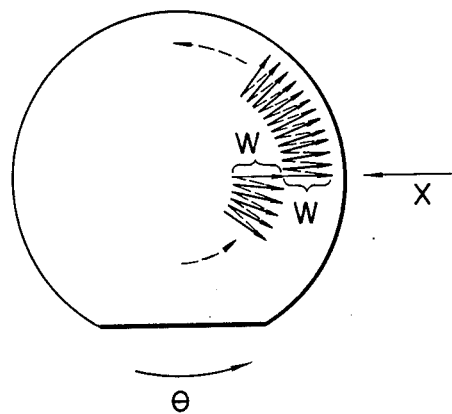
FIG. 5 shows a scanning pattern which is derived by the laser beam scanning apparatus shown in FIGS. 3 and 4.

For the examination, stage 20, on which semiconductor wafer 11 is mounted, is rotated at a constant speed in the $\theta$ direction by drive motor 22. The scan of the laser beam is started from the inner peripheral side of wafer 11 as shown in FIG. 5 by polygon mirror 26. The line scan is repeatedly executed with swing width W along the X direction on the semiconductor wafer surface. At this time, the laser beam is diffused and reflected on the surface of wafer 11 and a part of the laser beam is detected by detector 32. Detector 32 generates an output signal corresponding to an amount of light of the laser beam received. This output signal is sampled by a sampling signal synchronized with the scan of the laser beam from the position control. Thus, the peak value of the laser beam corresponding to the coordinates on the semiconductor wafer can be obtained. The level of this peak value is determined and then it is processed as informtion of a particle diameter by the CPU so as to correspond to each coordinate position and is then displayed on the display unit. This single line scan of the laser beam is finished for the period of time when stage 20 rotates by the predetermined angle of $\Delta\theta$. This line scan is repeatedly executed until stage 20 has rotated once. After the line scan of swing width W in the radial direction of semiconductor wafer 11 is executed for the period of time of one rotation of the semiconductor wafer as described above, a drive signal is supplied to the pulse motor from the position control of control system 40, thereby moving stage 20 by predetermined distance W in the X direction. Thereafter, the annular or peripheral region which is located outside the preceding scanning peripheral region by distance W is rectilinearly scanned under almost the same condition as the preceding scanning operation. However, in this case, to set the interval between scanning lines in each peripheral region to a constant value, it is also possible to execute the line scan each time stage 20 rotates by an angle smaller than $\Delta\theta$, thereby executing the line scan more times for one rotation in the case of scanning the outer peripheral region, as compared with the case of scanning the inner peripheral region. Whenever the line scan in the radial direction for the peripheral region of one circumference is finished in this manner, stage 20 is moved in the X direction or outwardly by predetermined distance W, thereby sequentially executing the line scan for the whole surface of wafer 11 from the innermost peripheral region to the outermost peripheral region. A part of the line scan pattern obtained in this manner is illustrated in FIG. 5. As described above, the beam spot sequentially scans on the line segments of swing width W along the circumferential direction of wafer 11 and scans the whole surface of wafer 11. Thus, the beam spot scans so as to draw substantially the same locus as the spiral locus. On the other hand, it is sufficient that swing width W of beam is shorter than the diameter of wafer 11. When the spot diameter was focused to, e.g., 10 μm to obtain the detecting sensitivity of 0.1 μmφ, the optimum swing width of laser beam is set to 10 to 15 mm. In the case of swing width W of such a value, the beam which was swung by polygon mirror 26 is uniformally focused by focusing lens system 30. Even if the position changes by the beam scan, a beam shape and a beam spot diameter are not changed, so that the uniform detecting sensitivity of the wafer surface is obtained.

As in the foregoing embodiment, according to the scanning method whereby the laser beam, focused so as to have the spot diameter of 10 μm, is repeatedly rectilinearly scanned at the swing width of, e.g., 15 mm by polygon mirror 26 and a nearly spiral beam scanning of the whole surface of the wafer is performed, the scanning time for a wafer having a diameter of six inches was merely 30 seconds in the case where the rotational speed of polygon mirror 26 was 2000 r.p.m. In addition, a change in beam spot diameter at this time was within a range of ±10%. On the other hand, when the beam scan was performed under the same condition as above by the spiral scanning method in the conventional example, the time required to scan the whole surface of the wafer was about five minutes. As compared with this conventional method, the scanning time according to the method of the foregoing embodiment was reduced to about 1/10.

The laser beam scanning apparatus which is used by the laser beam scanning method as mentioned above is mainly constituted by: stage 20 for moving the semiconductor wafer in rotational direction θ and in constant direction X perpendicular thereto; and polygon mirror 26 for repeating the line scan of the laser beam at constant swing width W. Both the mechanical and optical systems can be accomplished at fairly simple technical levels, so that this apparatus can be realized at a relatively low cost.

The present invention is not limited to the foregoing embodiment but the scan may be started from the outermost peripheral region and the wafer may be moved in the direction opposite to constant direction X or inwardly for each rotation of the semiconductor wafer.

On the other hand, it is also possible to scan the beam onto the whole surface of the wafer at an almost uniform density by changing the rotational speed of wafer 11 or polygon mirror 26 in dependence on whether the beam scanning position on the wafer surface is located on the outer peripheral side of the wafer or on the inner peripheral side of the wafer.

Although stage 20 has been moved by predetermined distance W in predetermined direction X each time stage 20 has rotated a full turn in the foregoing embodiment, for example, stage 20 may be also moved by a predetermined distance shorter than predetermined distance W.

What is claimed is:

1. An apparatus for scanning a laser beam to examine the surface of a semiconductor wafer comprising:
    a stage onto which a semiconductor wafer is mounted;
    driving means for rotating said semiconductor wafer and for moving the semiconductor wafer by only a predetermined distance in a predetermined direction every rotation of said wafer; and
    laser beam scanning means for repeatedly rectilinearly scanning the laser beam at a swing width of a predetermined amount in a direction perpendicular to the rotational direction of the semiconductor wafer.

2. A scanning apparatus according to claim 1, wherein said laser beam scanning means includes: laser beam generating means; a polygon mirror which is rotated at a constant speed and reflects the laser beam from said laser beam generating means; and a lens system for focusing the laser beam reflected by said polygon mirror onto the semiconductor wafer.

3. A scanning apparatus according to claim 2, wherein said polygon mirror and said lens system are arranged so as to scan the laser beam by said predetermined distance on the line which passes through the rotational center of said stage.

4. A method of scanning a laser beam to examine the surface of a semiconductor wafer comprising the steps of:
    rotating a semiconductor wafer;
    repeatedly rectilinearly scanning a laser beam on the surface of the semiconductor wafer at a constant swing width in a direction perpendicular to the rotational direction of the semiconductor wafer; and
    moving the semiconductor wafer by a predetermined distance along said scanning direction each time the semiconductor wafer rotates once.

5. A scanning method according to claim 4, wherein said laser beam is scanned at a swing width equal to said predetermined distance on the line which passes through the rotational center of said semiconductor wafer.

* * * * *